US008240684B2

(12) United States Patent
Ross et al.

(10) Patent No.: US 8,240,684 B2
(45) Date of Patent: Aug. 14, 2012

(54) MEDICAL VENTILATOR CART (75) Inventors: Christopher G. Ross, Del Mar, CA (US); Richard Calou, San Diego, CA (US); Colt Sander, Alvo, NE (US); Tony L. Lee, New Berlin, WI (US); Christian J. Stefanovitz, West Bend, WI (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 320 days.

(21) Appl. No.: 12/631,636

(22) Filed: Dec. 4, 2009

(65) Prior Publication Data
US 2010/0148458 A1    Jun. 17, 2010

Related U.S. Application Data (60) Provisional application No. 61/122,284, filed on Dec. 12, 2008.

(51) Int. Cl.
*B62B 3/00* (2006.01)
(52) U.S. Cl. .................. 280/47.34; 280/79.11
(58) Field of Classification Search ............. 280/47.34, 280/47.35, 79.11, 79.2; D24/164, 183, 185, D24/186, 232, 234
See application file for complete search history.

(56) References Cited

U.S. PATENT DOCUMENTS

| | | | |
|---|---|---|---|
| 3,224,720 A | 12/1965 | Hain | |
| 3,565,384 A | 2/1971 | Lionel | |
| D222,527 S | 11/1971 | Ziaylek | |
| 3,970,344 A | 7/1976 | Baumann | |
| D245,929 S | 9/1977 | Montambo | |
| D252,121 S | 6/1979 | Rutherford | |
| 4,213,592 A | 7/1980 | Lingenfeiser | |
| 4,213,648 A | 7/1980 | Steichen | |
| 4,294,481 A | 10/1981 | Pearl | |
| D281,951 S | 12/1985 | LaMeyer et al. | |
| 4,696,420 A | 9/1987 | Kullk | |
| D307,494 S | 4/1990 | Goodnight | |
| D319,003 S | 8/1991 | Scharrenberg | |
| 5,170,804 A | 12/1992 | Glassman | 128/849 |

(Continued)

FOREIGN PATENT DOCUMENTS

DE     102 11 365 A1    10/2003

(Continued)

OTHER PUBLICATIONS

PCT Notification of Transmittal of the International Search Report and the Written Opinion of the International Searching Authority, or the Declaration, Date of Mailing: May 17, 2010, International Application No. PCT/US2009/066864, International Filing Date: Apr. 12, 2009, Applicant: Nellcor Puritan Bennett LLC.

*Primary Examiner* — John Walters (57) ABSTRACT

A medical ventilator cart, for use in hospitals or other medical settings, stores and transports various components of a ventilator system, such as a Breath Delivery Unit, a display monitor, and a compressor. First and second platforms are suspended above a base of the cart and allow the various ventilator cart components to be separately and independently placed on and removed from the cart without the need to move or rearrange any of the other ventilator components. One version of the cart provides an additional compressor platform attached to the base for mounting a compressor below the first platform.

19 Claims, 8 Drawing Sheets

U.S. PATENT DOCUMENTS

| | | | |
|---|---|---|---|
| 5,191,679 A | 3/1993 | Harper | |
| 5,340,140 A | 8/1994 | Bynum | |
| 5,518,310 A | 5/1996 | Ellman et al. | 312/249.12 |
| D372,189 S | 7/1996 | Andis et al. | |
| D389,917 S * | 1/1998 | Hornback et al. | D24/186 |
| D394,381 S | 5/1998 | Ziaylek et al. | |
| D411,651 S | 6/1999 | Fougerousse | |
| 6,102,497 A * | 8/2000 | Ehr et al. | 312/209 |
| D447,567 S | 9/2001 | Murphy et al. | D24/172 |
| D459,477 S * | 6/2002 | Stocks et al. | D24/164 |
| 6,419,654 B1 * | 7/2002 | Kadan | 604/27 |
| 6,626,445 B2 | 9/2003 | Murphy et al. | 280/47.34 |
| 6,669,224 B2 * | 12/2003 | Newkirk | 280/508 |
| 6,669,639 B1 | 12/2003 | Miller et al. | 600/443 |
| D486,915 S | 2/2004 | Warschewske et al. | D24/185 |
| D492,856 S | 7/2004 | Rossini et al. | D6/426 |
| D493,042 S * | 7/2004 | Rossini et al. | D6/426 |
| D493,977 S | 8/2004 | Rossini et al. | D6/426 |
| D494,049 S | 8/2004 | Ziaylek et al. | |
| D500,575 S | 1/2005 | Lucas | D34/12 |
| D503,832 S | 4/2005 | Kennon | |
| 6,980,419 B2 | 12/2005 | Smith et al. | 361/679.41 |
| D518,267 S | 3/2006 | Arceta | D34/14 |
| 7,009,840 B2 * | 3/2006 | Clark et al. | 361/679.41 |
| D522,180 S | 5/2006 | Goria, II | |
| D528,904 S | 9/2006 | Reding | |
| D534,746 S | 1/2007 | Rossini et al. | D6/495 |
| D535,509 S | 1/2007 | Rossini et al. | D6/511 |
| D539,794 S | 4/2007 | Rossini et al. | 14/302 |
| D544,962 S * | 6/2007 | Diener et al. | D24/186 |
| D548,918 S | 8/2007 | Nussberger | D34/17 |
| 7,287,735 B2 | 10/2007 | Heerdt et al. | |
| 7,352,570 B2 | 4/2008 | Smith et al. | 361/679.41 |
| D590,107 S | 4/2009 | Poulin | |
| D601,076 S | 9/2009 | Ziaylek | |
| 7,594,668 B2 | 9/2009 | Arceta et al. | 280/47.35 |
| D618,356 S | 6/2010 | Ross | |
| 2005/0288571 A1 | 12/2005 | Perkins et al. | 600/407 |
| 2006/0107463 A1 * | 5/2006 | Foster et al. | 5/620 |
| 2008/0055826 A1 | 3/2008 | Smith et al. | 361/679.23 |

FOREIGN PATENT DOCUMENTS

| | | |
|---|---|---|
| WO | 00/69387 A1 | 11/2000 |
| WO | 2006/020862 A2 | 2/2006 |

* cited by examiner

MEDICAL VENTILATOR CART

REFERENCE TO RELATED APPLICATION

This application claims the benefit of U.S. Provisional Application Ser. No. 61/122,284, filed on Dec. 12, 2008, the disclosure of which is incorporated herein by reference in its entirety.

COPYRIGHTS

All rights, including copyrights, in the material included herein are vested in and the property of the Applicants. The Applicants retain and reserve all rights in the material included herein, and grant permission to reproduce the material only in connection with reproduction of the granted patent and for no other purpose.

BACKGROUND

The present invention is directed to carts or cart transport systems for use with medical ventilators. Medical ventilators typically include a large number of associated components including a Breath Delivery Unit ("BDU"), a display, a compressor, a battery back-up device, and additional peripheral components. When the ventilator components are placed on a wheeled cart to provide mobility, the components are often stacked upon one another so that components in the middle or at the bottom of the stack cannot be easily removed. For example, the display may be placed atop the BDU, which in turn may be placed atop a compressor or battery back-up device. In this alignment, replacement of a faulty compressor first requires removal of the display and BDU components, thereby increasing the amount of work (and prolonging the time) required to replace the faulty component. Such delays may prove detrimental to patient care, particularly in a busy hospital setting.

A further drawback to stacking ventilator components on top of each other on a wheeled cart is that a user often moves (i.e., pulls or pushes) the cart by grasping one of the stacked components (e.g., the display at the top of the stack). While wheeled carts often provide one or more handles, such handles are often located on the side of the cart (to provide for stacking the components between the handles), and thus a user may be tempted to pull one of the ventilator components in lieu of reaching for the supplied handle.

It is with respect to these considerations and others that the present invention has been made.

SUMMARY

This summary is provided to introduce a selection of concepts in a simplified form that are further described below in the detailed description. This summary is not intended to identify key features or essential features of the claimed subject matter. Nor is this summary intended to be used to limit the claimed subject matter's scope.

It is an object of the present invention to provide improved medical ventilator carts for use in a hospital or other medical environment. Embodiments of the medical ventilator carts disclosed herein may be designed to retain, store, and operate various ventilator components and allow for ease of movement or transport of such components in hospitals or other medical settings. For instance, a medical ventilator cart for supporting components of a ventilator system is disclosed, and in some embodiments, the medical ventilator cart may comprise a base comprising a plurality of wheels, a first vertical support attached to the base and a first ventilator component platform, and a second vertical support attached to a second ventilator component platform and further attached to one of the first ventilator component platform and the first vertical support.

In other embodiments, another medical ventilator cart for supporting components of a ventilator system is provided. In these embodiments, the medical ventilator cart may comprise a "+" shaped base comprising a plurality of wheels; a first vertical support attached to the base and a first ventilator component platform, wherein the first vertical support extends from a center of the base; and a second vertical support attached to the first ventilator component platform and a second ventilator component platform, wherein the second vertical support extends from a rear portion of the first ventilator component platform.

Yet, in other embodiments, a medical ventilator cart for supporting components of a ventilator system comprising the following is provided: a "U" shaped base comprising a plurality of wheels; a first vertical support attached to the base and a first ventilator component platform, wherein the first vertical support extends from a rear end of the base; and a second vertical support attached to the first vertical support and a second ventilator component platform, wherein the second vertical support is positioned to the rear of the first ventilator component platform; and wherein the base further includes a compressor platform adapted to mount a compressor below the first ventilator component platform.

Both the foregoing summary and the following detailed description are illustrative and explanatory only. Accordingly, the disclosure of the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

The accompanying drawings, which are incorporated in and constitute a part of this disclosure, illustrate various embodiments of the present invention. In the drawings.

DETAILED DESCRIPTION

The following detailed description refers to the accompanying drawings. Wherever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings. Accordingly, the following detailed description does not limit the invention.

In some embodiments of the invention, medical ventilator carts for use in hospital or other medical settings are provided. In further embodiments, these medical ventilator carts may comprise various components of a ventilator system. Such components may include, but are not limited to, a Breath Delivery Unit ("BDU"), a display monitor, a compressor, and combinations of two or more of these components. In this disclosure, the main ventilator component is referred to as a Breath Delivery Unit, and will be abbreviated "BDU" throughout this disclosure.

Embodiments of the invention may include medical ventilator carts designed for different hospital or medical uses, such as, for instance, a compressorless ventilator cart (e.g., for use in neonatal applications) and a compressor-mount ventilator cart (e.g., for use with adult patients). The compressor-mount ventilator cart may comprise three removable components: a BDU, a display monitor, and a compressor. The compressorless ventilator cart may comprise two removable components: a BDU and a display monitor. Generally, the compressorless medical ventilator cart does not provide for the inclusion of a compressor since it may be used in a neonatal application or in a quiet hospital or medical setting where the noise of the compressor may be objectionable.

Ventilator carts consistent with embodiments of the invention may allow ventilator components—e.g., a BDU, a display monitor, a compressor, etc.—to be separately and independently removed from the cart without the need to remove any of the other ventilator components. Likewise, the ventilator carts may allow ventilator components to be separately and independently placed onto the cart without the need to move or rearrange any of the other ventilator components already present on the cart. Accordingly, in embodiments consistent with the invention, ventilator components are not placed on top of and supported by other ventilator components in a stacking configuration.

Referring now to the drawings, FIGS. 1-4 illustrate a compressorless medical ventilator cart 100 provided in an embodiment of the invention. A compressorless ventilator cart 100 may comprise any suitable base that provides stability and maneuverability to the cart. For instance, a "+" shaped base or a "U" shaped base of sufficient dimension to prevent the cart from tipping over may be employed. Generally, the base will be equipped with wheels or casters to allow ease or maneuverability or transport. In FIGS. 1-4, the compressorless ventilator cart 100 comprises a "+" shaped base 105 with four casters 110 attached to the distal ends of the "+" shaped base 105. The casters 110 may swivel or rotate and, in some embodiments, may be equipped with a braking mechanism. A central support post 130 is preferably attached to the center of the "+" shaped base 105. The central support post 130 supports a weight-bearing BDU platform 135 designed to hold and support a BDU 140. In some embodiments, the central support post 130 may be adjustable in height depending on the end-use and the requirements of the compressorless ventilator cart 100 in the hospital or medical setting. The BDU platform 135 may be sized so that the BDU 140 may be easily placed on the platform 135 and shaped so that the BDU 140 may be held securely in position on the compressorless ventilator cart 100.

Figure 3:
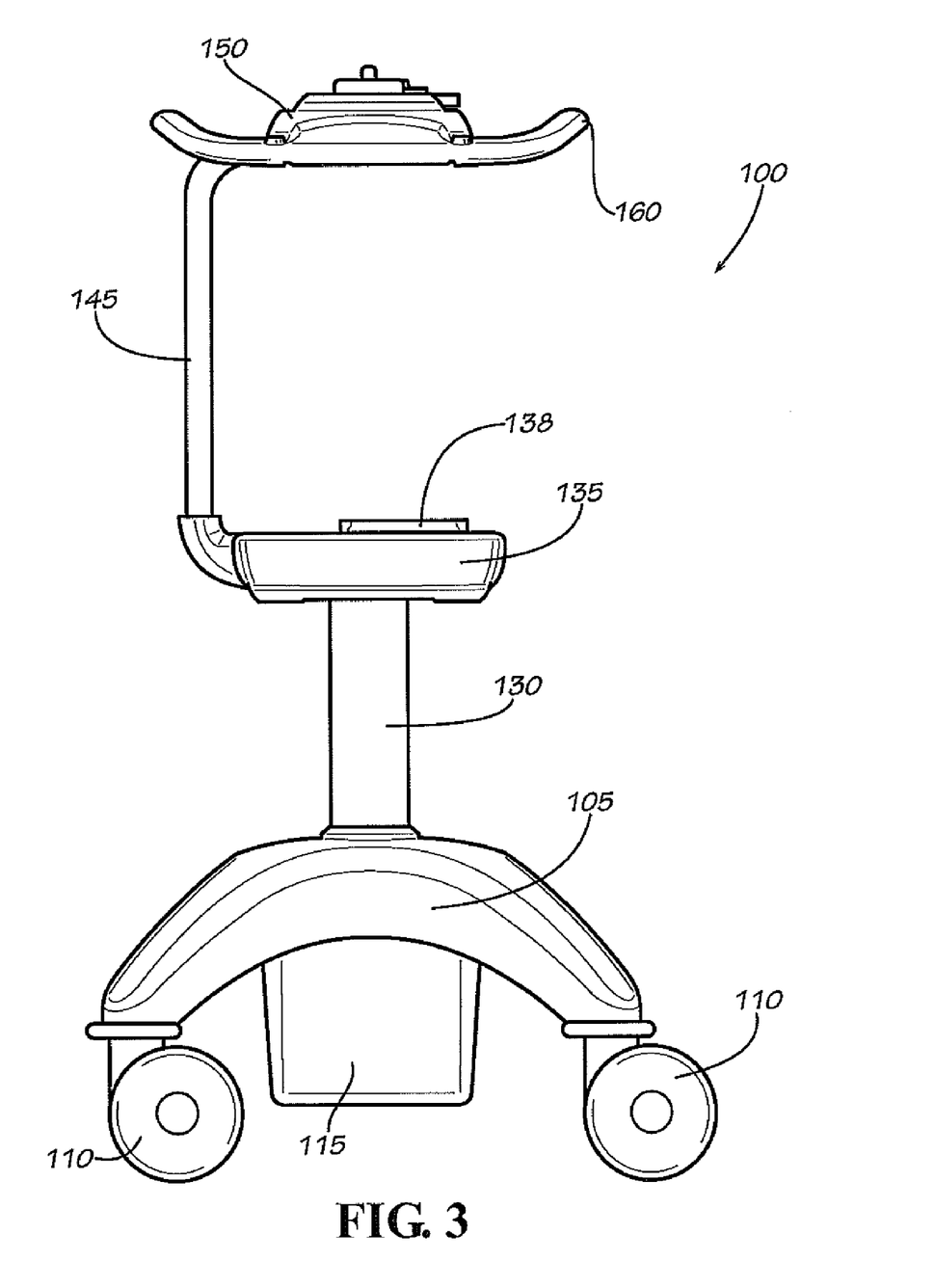
FIG. 3 illustrates a right side elevation view of the compressorless medical ventilator cart of FIG. 1 without ventilator components.
Figure 4:
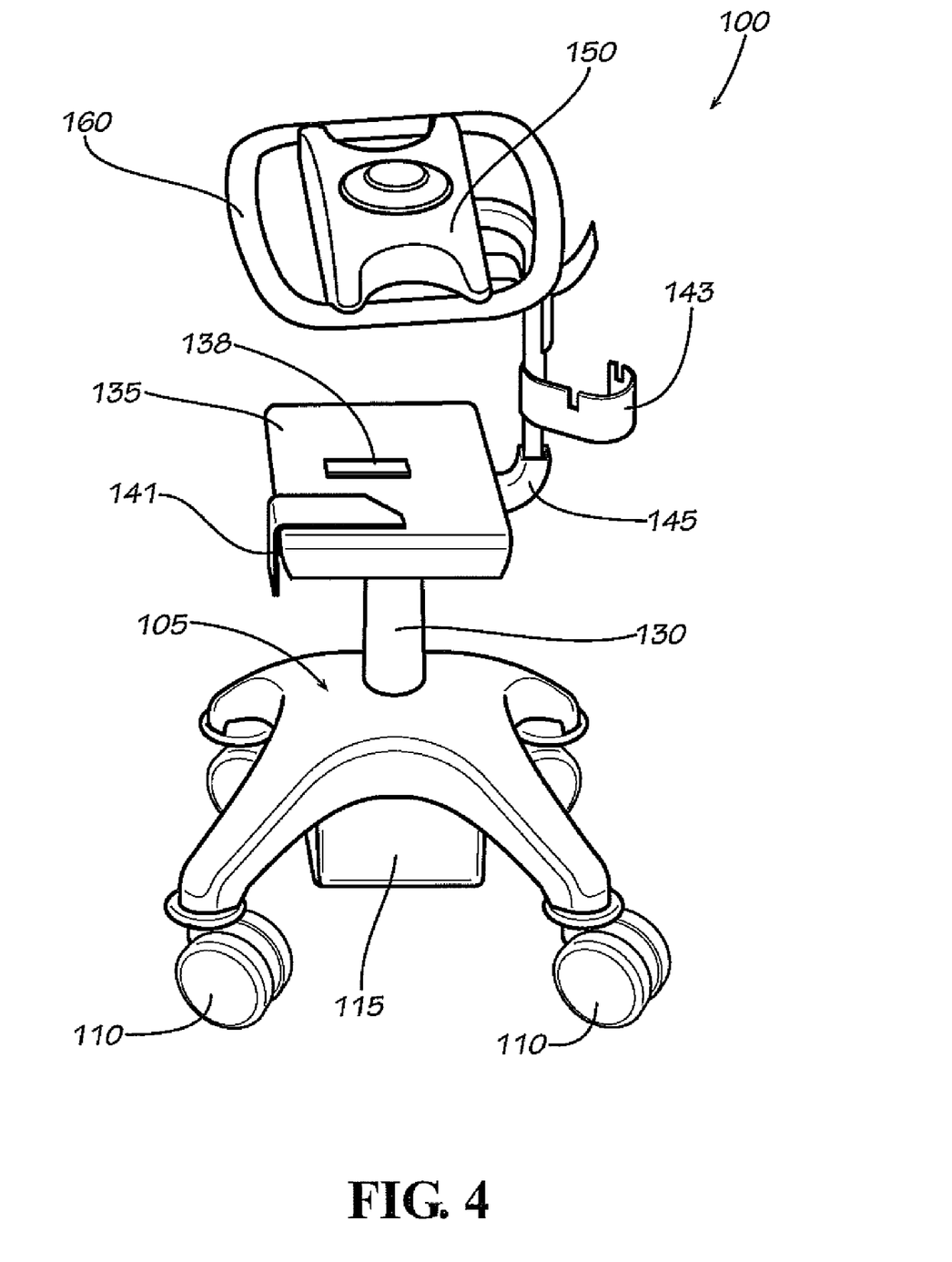
FIG. 4 illustrates a left side perspective view of a compressorless medical ventilator cart without ventilator components provided in an embodiment of the invention.

For improved stability on the compressorless ventilator cart 100, the BDU 140 may have a recessed area or groove that fits on a rail 138 attached to the BDU platform 135. The location of the rail 138 on the BDU platform 135 is illustrated in FIGS. 3-4. Referring now to FIG. 4, in embodiments of the invention, a humidifier bracket 141 may be attached near one side of the BDU platform 135, where the humidifier bracket preferably defines an inverted "L" shape. In one embodiment, the humidifier bracket 141 supports a humidifier (not shown), where the humidifier is designed to add moisture to the air or oxygen being supplied via the BDU 140.

Figure 2:
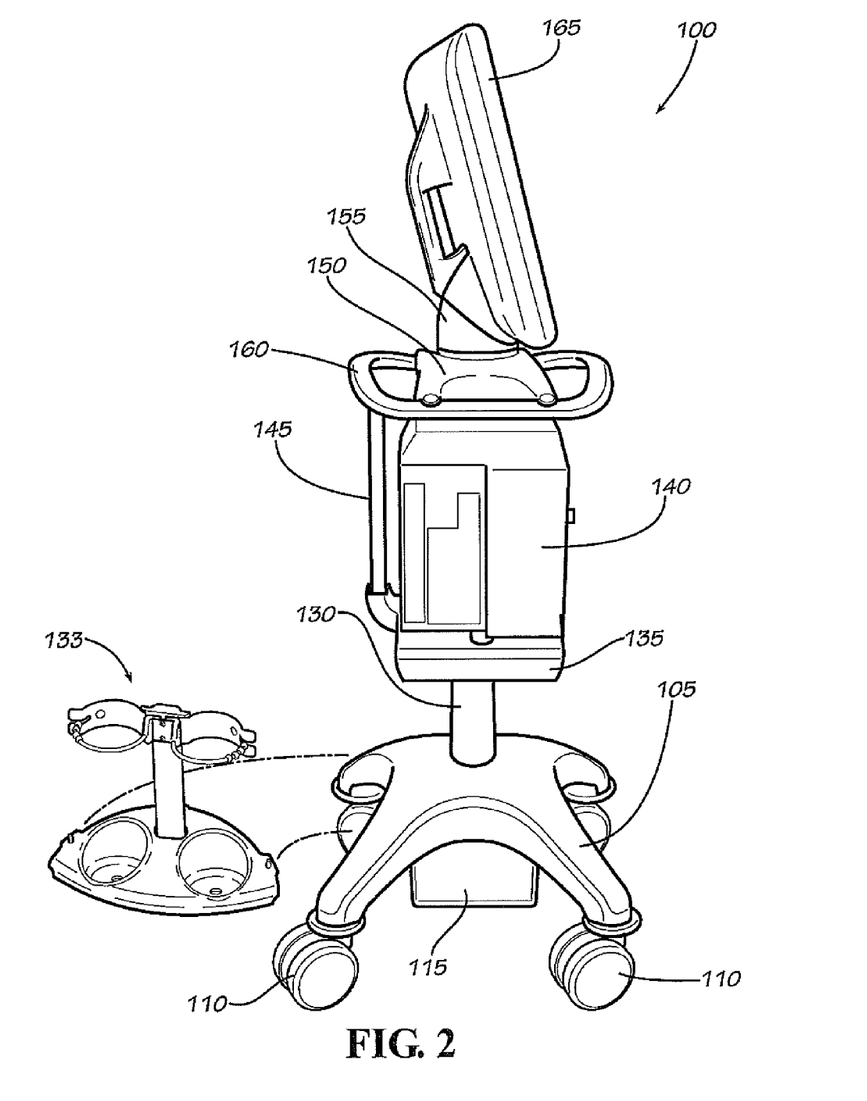
FIG. 2 illustrates a right side perspective view of the compressorless medical ventilator cart of FIG. 1, with a cylinder mount accessory shown exploded outward from a base of the cart.

The BDU platform 135, in addition to being supported by the central support post 130, may be attached to another support, a spine support 145. As illustrated in FIGS. 2-4, the base or bottom of the spine support 145 may be attached at the rear of the BDU platform 135. In one embodiment, the spine support 145 connects to and supports a second weight-bearing platform, often referred to as a display platform 150. Optionally, a water trap bracket 143 may be affixed to the spine support 145, as shown in FIG. 4. The water trap bracket 143 may support a wall air water trap (not shown). A hospital or wall air line may be an inlet to the wall air water trap, and the outlet of the wall air water trap may be attached to the BDU 140.

A display monitor 165 for the ventilator BDU 140 is preferably attached or mounted on the display platform 150. The display monitor 165 may be attached to the display platform 150 with a swivel mount 155 which allows the display monitor 165 to be rotated for easy positioning and viewing by a user of the ventilator cart 100. The spine support 145 is of sufficient height to permit the BDU 140 to be removed easily without interference or encumbrance from the display platform 150. It is contemplated that the spine support 145 may have an adjustable height to facilitate the use of various sizes of BDU's, or for other end-use or ergonomic requirements of the compressorless ventilator cart 100 in the hospital or medical setting. Further, the rear positioning of the spine support 145 on the compressorless ventilator cart 100 allows easy placement of the BDU 140 onto, or removal of the BDU 140 from, the BDU platform 135.

A cart handgrip 160 preferably encircles the display platform 150, as illustrated in FIGS. 2 and 4. The cart handgrip 160 may allow easy grasping and control of the compressorless ventilator cart 100 from any side of the cart, whether from the front, either side, or the back. The cart handgrip 160 preferably extends entirely around the display platform 150 and, in one embodiment, is shaped without any sharp corners. The cart handgrip 160 may be designed to prevent the cart handgrip 160 from being caught on other surfaces or objects. Further, the cart handgrip 160 may be larger in circumference than a width dimension of the BDU 140, thereby reducing the likelihood that the BDU 140 will be struck or damaged by movements of the user of the compressorless ventilator cart 100, or during transport of the cart 100 itself. The cart handgrip 160 also may improve the maneuverability of the compressorless ventilator cart 100 by allowing it to be pushed/pulled from any position or side of the cart. In some embodiments, the width and/or length of the cart handgrip 160 may be smaller than the width and/or length of the "+" shaped base 105, though this is not a requirement.

In one preferred embodiment, the cart handgrip 160 is attached to a plurality of arms extending from the display platform 150, wherein the arms attach to multiple locations along the circumference of the substantially circular handgrip 160 to allow sufficient space for a user's hand to reach and grab the cart handgrip 160 without disturbing the display monitor 165 or the BDU 140. In an alternative embodiment (not shown), the spine support 145 may be directly connected to a rear portion of the substantially circular cart handgrip 160, while the arms of the display platform 150 are again attached to the handgrip 160 to support the display monitor 165 above the handgrip 160.

Figure 1:
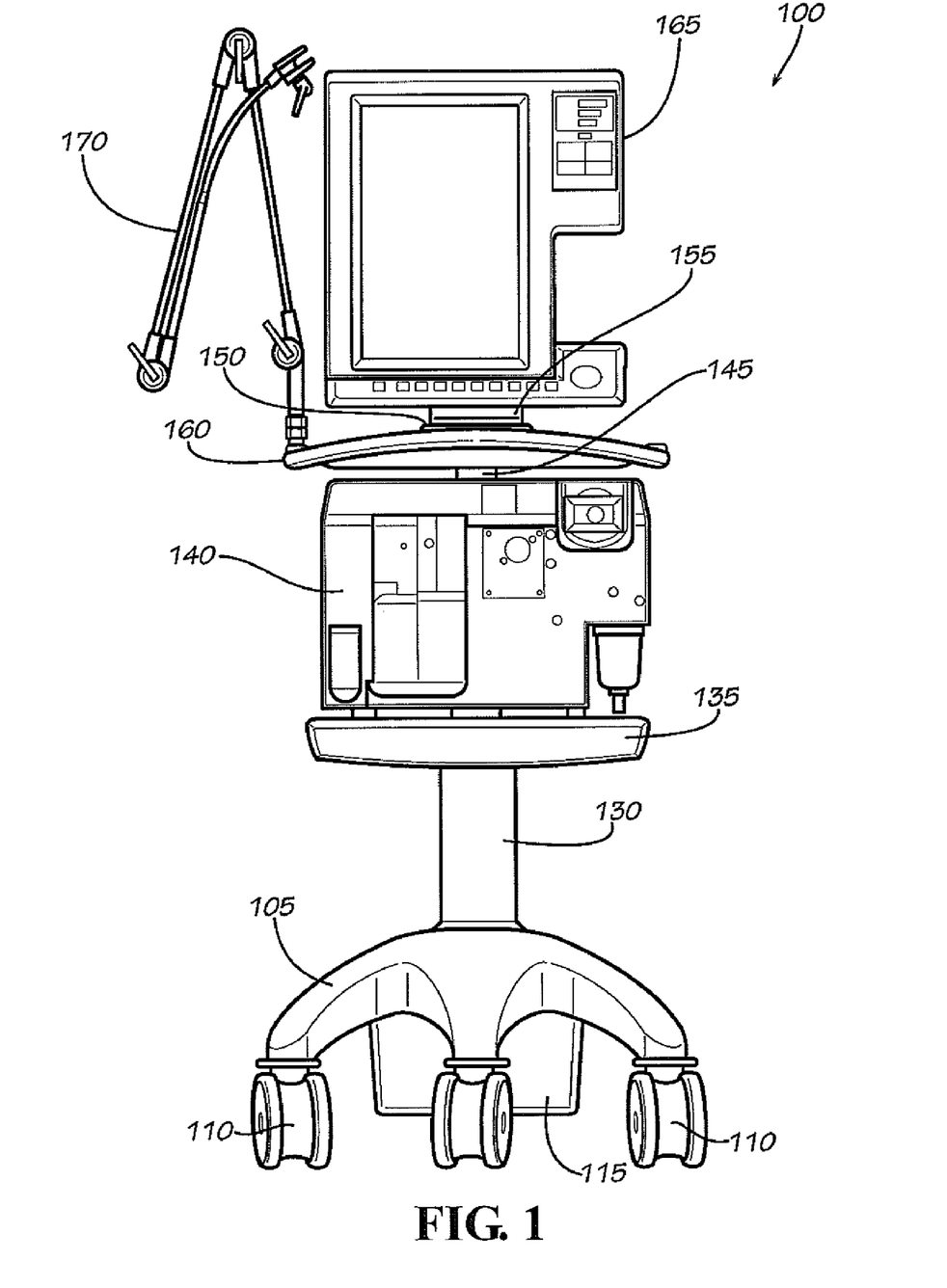
FIG. 1 illustrates a front view of a compressorless medical ventilator cart containing ventilator components provided in an embodiment of the invention.

Consistent with embodiments of the invention, an extendable arm 170 may be removably attached to the display platform 150, illustrated on the left side of the display monitor 165 in the front view of FIG. 1. The extendable arm 170 may be removably attached to any position on the display platform 150 or, alternatively, to any position on the cart handgrip 160. The extendable arm 170 may be provided with one or more clips or pegs to which papers, clip boards, ventilator tubing or other equipment may be removably attached to the compressorless ventilator cart 100. It is contemplated that more than one extendable arm 170 may be utilized with the ventilator cart 100.

The compressorless ventilator cart 100 optionally may contain a battery housing 115 positioned under the "+" shaped base 105. The battery housing 115 provides additional weight for added stability of the compressorless ventilator cart 100, and also permits the cordless use of the compressorless ventilator cart 100, e.g., without a power cord attached to an electrical socket/power supply (not shown). The battery housing 115 may contain a battery (not shown) that provides a back-up power supply to the compressorless ventilator cart 100 for a time period of up to about 6 hours, such as, for example, from about 1 hour to about 4 hours. The battery in the battery housing 115 may connect to the BDU 140 via a cable that extends through the central support post 130.

Consistent with embodiments of this invention, the compressorless ventilator cart 100 optionally may comprise a cylinder mount 133, as illustrated in FIG. 2. The cylinder mount 133 may be attached to the rear arch section of the "+" shaped base 105 between the two rear wheels or casters 110. The cylinder mount 133 may be designed to hold one or two gas cylinders, e.g., compressed air or oxygen (gas cylinders not shown). Hence, the BDU 140 on the compressorless ventilator cart 100 may be operated without access to an external electrical power supply and without access to an external hospital or wall air/oxygen line.

Referring now to FIGS. 5-8, a compressor-mount medical ventilator cart 200 provided in another embodiment of the invention is illustrated. The compressor-mount ventilator cart 200 may comprise any suitable base that provides stability and maneuverability to the cart. For instance, a "+" shaped base or a "U" shaped base of sufficient dimension to prevent the cart from tipping over may be employed. Generally, the base will be equipped with wheels or casters to allow ease or maneuverability or transport, but this is not a requirement. In FIGS. 5-8, the compressor-mount ventilator cart 200 comprises a "U" shaped base 205 with four casters 210 attached to the "U" shaped base 205 as illustrated. The casters 210 may swivel or rotate and, in some embodiments, may be equipped with a braking mechanism.

In one embodiment, the "U" shaped base 205 includes a compressor platform 220 which supports a compressor 225. The compressor platform 220 is preferably sized so that the compressor 225 may be easily placed on the platform 220 and shaped so that the compressor 225 may be held securely in position on the ventilator cart 200. The compressor platform 220, upon which the compressor 225 is to be positioned, may be integral or part of the "U" shaped base 205 or, alternatively, may be separate and distinct from the "U" shaped base 205 for easy removal of the platform 220. The compressor 225 may have a lower portion 215.

In a preferred embodiment, a battery (not shown) may be located between the compressor 225 and a BDU 240, such as, for instance, attached to the underside of a BDU platform 235 that supports the BDU 240. The battery attached to the BDU platform 235 may permit the cordless use of the compressor-mount ventilator cart 200, e.g., without a power cord attached to an electrical socket/power supply (not shown). The battery may provide back-up power supply to the compressor-mount ventilator cart 200 for a time period of up to about 6 hours, such as, for example, from about 1 hour to about 4 hours. In an alternate embodiment, the battery may be housed in lower portion 215, and positioned on the underside of the "U" shaped base 205. In this configuration, the battery may connect to the BDU 240 via a cable through a first spine support 230, described below.

A first spine support 230 may be attached to the rear of the "U" shaped base 205 or compressor platform 220. The first spine support 230 may support a weight-bearing BDU platform 235 designed to hold and support a BDU 240. The BDU platform 235 is preferably sized so that the BDU 240 may be easily placed on the platform 235 and shaped so that the BDU 240 may be held securely in position on the compressor-mount ventilator cart 200. The first spine support 230 is preferably of sufficient height to permit the compressor 225 to be removed easily without interference or encumbrance from the BDU platform 235. It is contemplated that the first spine support 230 may have an adjustable height to facilitate the use of various sizes of compressors, or for other benefits or requirements in the hospital or medical environment. Further, the rear positioning of the first spine support 230 on the compressor-mount ventilator cart 200 allows for easy placement of the compressor 225 onto, or removal of the compressor 225 from, the compressor platform 220 and/or the "U" shaped base 205.

Figure 8:
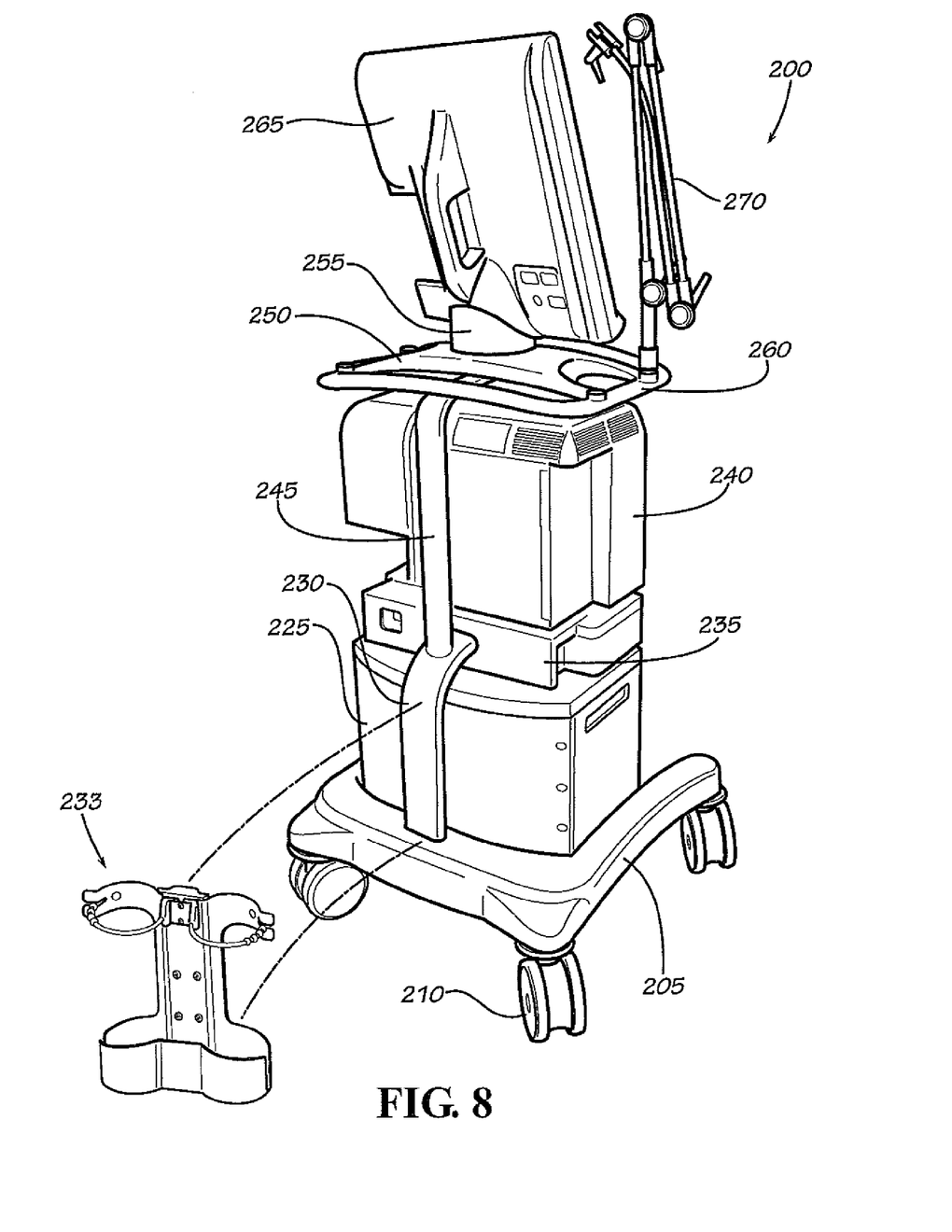
FIG. 8 illustrates a rear perspective view of the compressor-mount medical ventilator cart of FIG. 5, with a cylinder mount accessory shown exploded outward from the cart.

Consistent with embodiments of this invention, the compressor-mount ventilator cart 200 optionally may include a cylinder mount 233, as illustrated in FIG. 8. The cylinder mount 233 may be positioned on top of the compressor platform 220 and/or the "U" shaped base 205. The cylinder mount 233 may have a recessed center section to fit around the first spine support 230, and may be affixed to the support 230. The cylinder mount 233 may be designed to hold one or two gas cylinders, e.g., compressed air or oxygen (gas cylinders not shown). Hence, the BDU 240 on the compressor-mount ventilator cart 200 may be operated without access to an external electrical power supply and without access to an external hospital or wall air/oxygen line.

A second spine support 245 is preferably supported on either the first spine support 230 or the attached BDU platform 235. In a preferred embodiment illustrated in FIGS. 6-8, the second spine support 245 is attached directly to the first spine support 230. The second spine support 245 preferably connects to and supports another weight-bearing platform, often referred to as a display platform 250. A display monitor 265 for the ventilator BDU 240 may be attached or mounted on the display platform 250. The display monitor 265 may be attached to the display platform 250 with a swivel mount 255, which allows the display monitor 265 to be rotated for easy positioning and viewing by a user of the ventilator cart 200. The second spine support 245 may be of sufficient height to permit the BDU 240 to be removed easily without interference or encumbrance from the display platform 250. It is contemplated that the second spine support 245 may have an adjustable height to facilitate the use of various sizes of BDU's, or for other end-use or ergonomic requirements of the compressor-mount ventilator cart 200 in the hospital or medical setting. Further, the rear positioning of the second spine support 245 on the ventilator cart 200 allows for easy placement of the BDU 240 onto, or removal of the BDU 240 from, the BDU platform 235.

A cart handgrip 260 preferably encircles the display platform 250, as illustrated in FIG. 8. The cart handgrip 260 provides easy grasping and control of the compressor-mount ventilator cart 200 from any side of the cart, whether from the front, either side, or back. The cart handgrip 260 preferably extends entirely around the display platform 250 and, in one embodiment, is shaped without any sharp corners. The cart handgrip 260 may be designed to prevent the cart handgrip 260 from being caught on other surfaces or objects. Further, the cart handgrip 260 may be larger in circumference than a width dimension of the BDU 240, to reduce the likelihood that the BDU 240 may be struck or damaged by movements of the user of the compressor-mount ventilator cart 200, or during transport of the ventilator cart 200 itself. The cart handgrip 260 also may improve the maneuverability of the compressor-mount ventilator cart 200 by allowing it to be pushed/pulled from any position or side of the cart. In some embodiments, the width and/or length of the cart handgrip 260 may be smaller than the width and/or length of the "U" shaped base 205, though this is not a requirement.

In a preferred embodiment, the cart handgrip 260 is attached to a plurality of arms extending from the display platform 250, wherein the arms attach to multiple locations along the substantially circular handgrip 260 to allow sufficient space for a user's hand to reach and grab the cart handgrip 260 without disturbing the display monitor 265 or the BDU 240.

Figure 5:
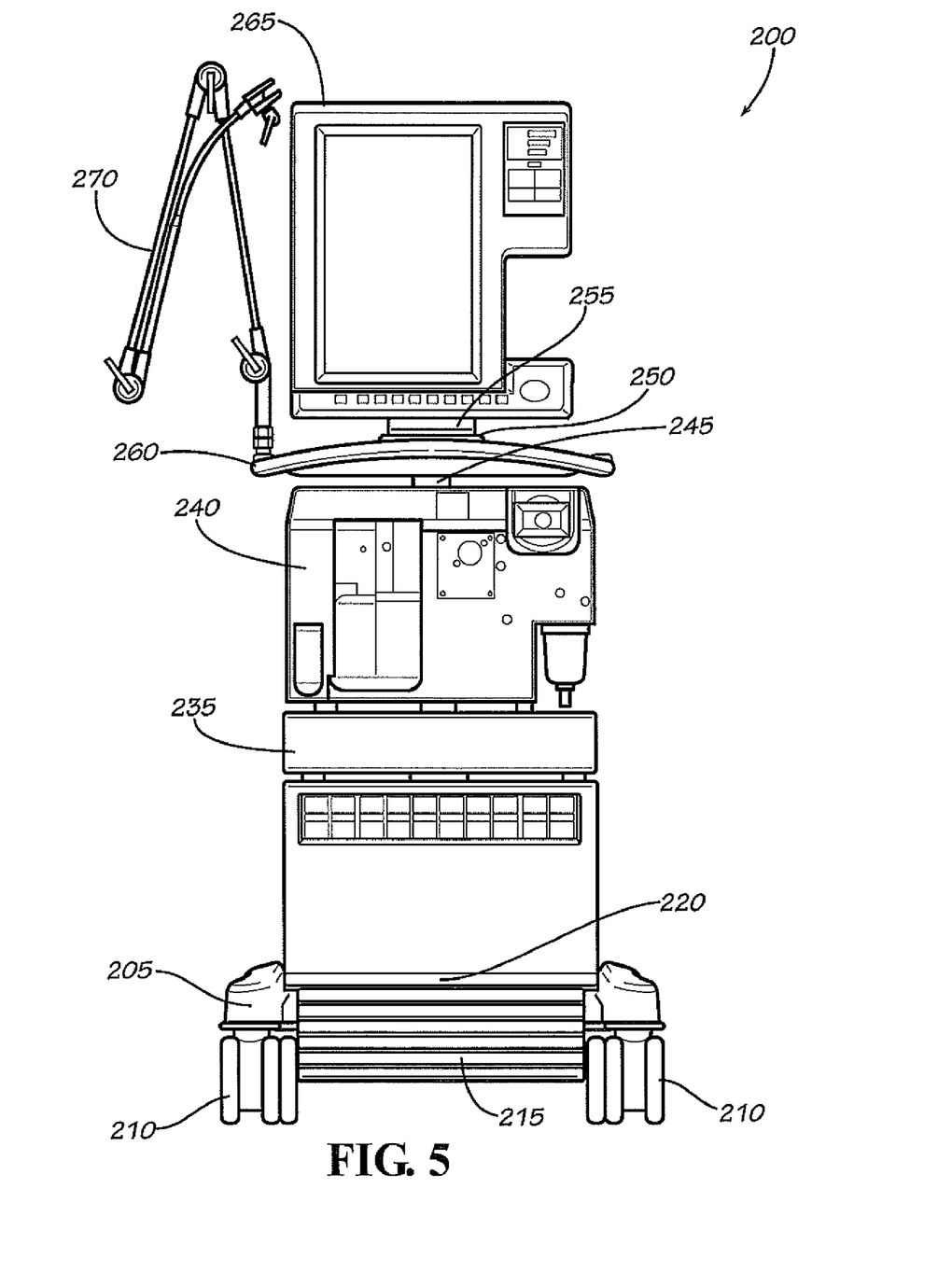
FIG. 5 illustrates a front view of a compressor-mount medical ventilator cart containing ventilator components provided in an embodiment of the invention.
Figure 6:
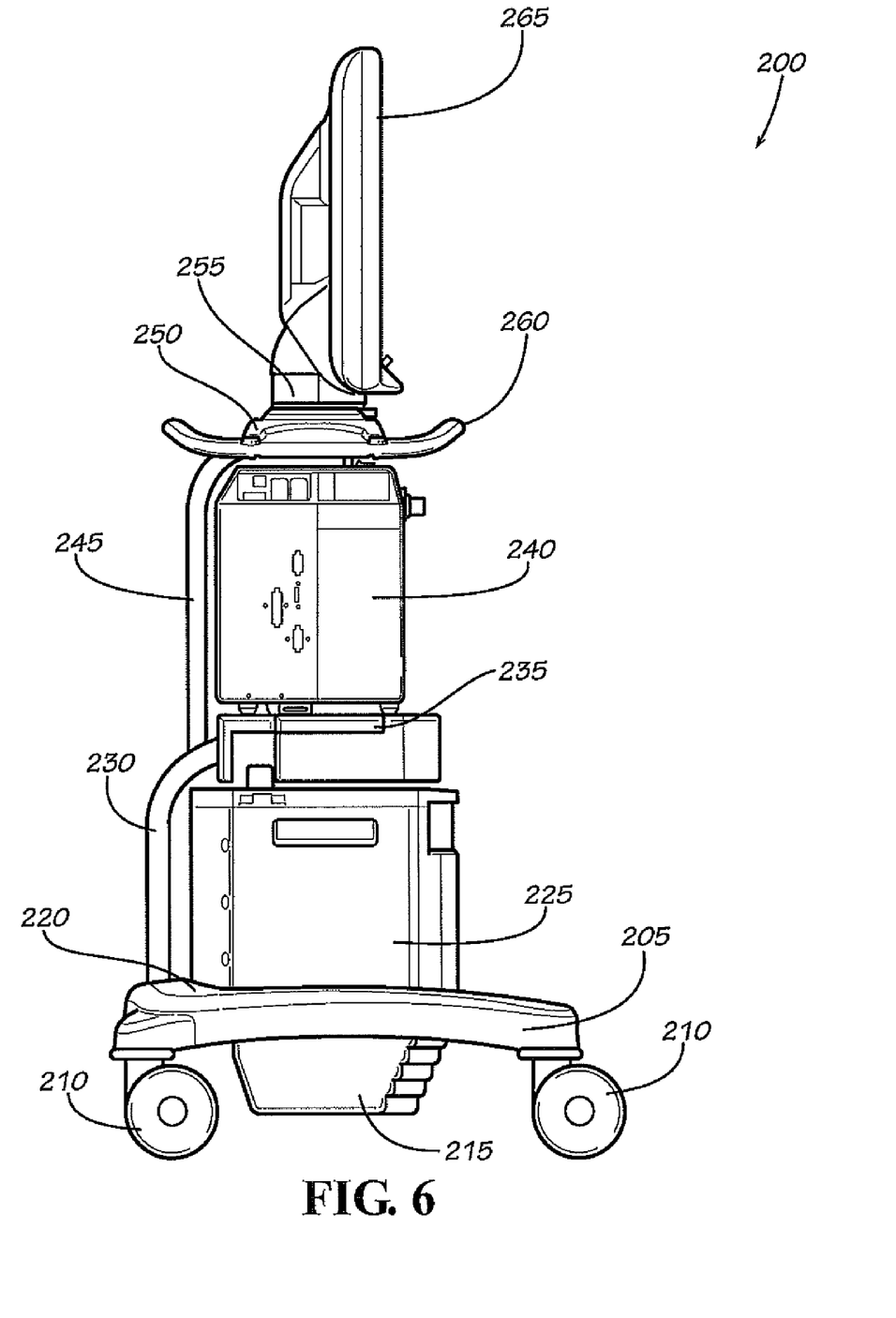
FIG. 6 illustrates a right side elevation view of the compressor-mount medical ventilator cart of FIG. 5.
Figure 7:
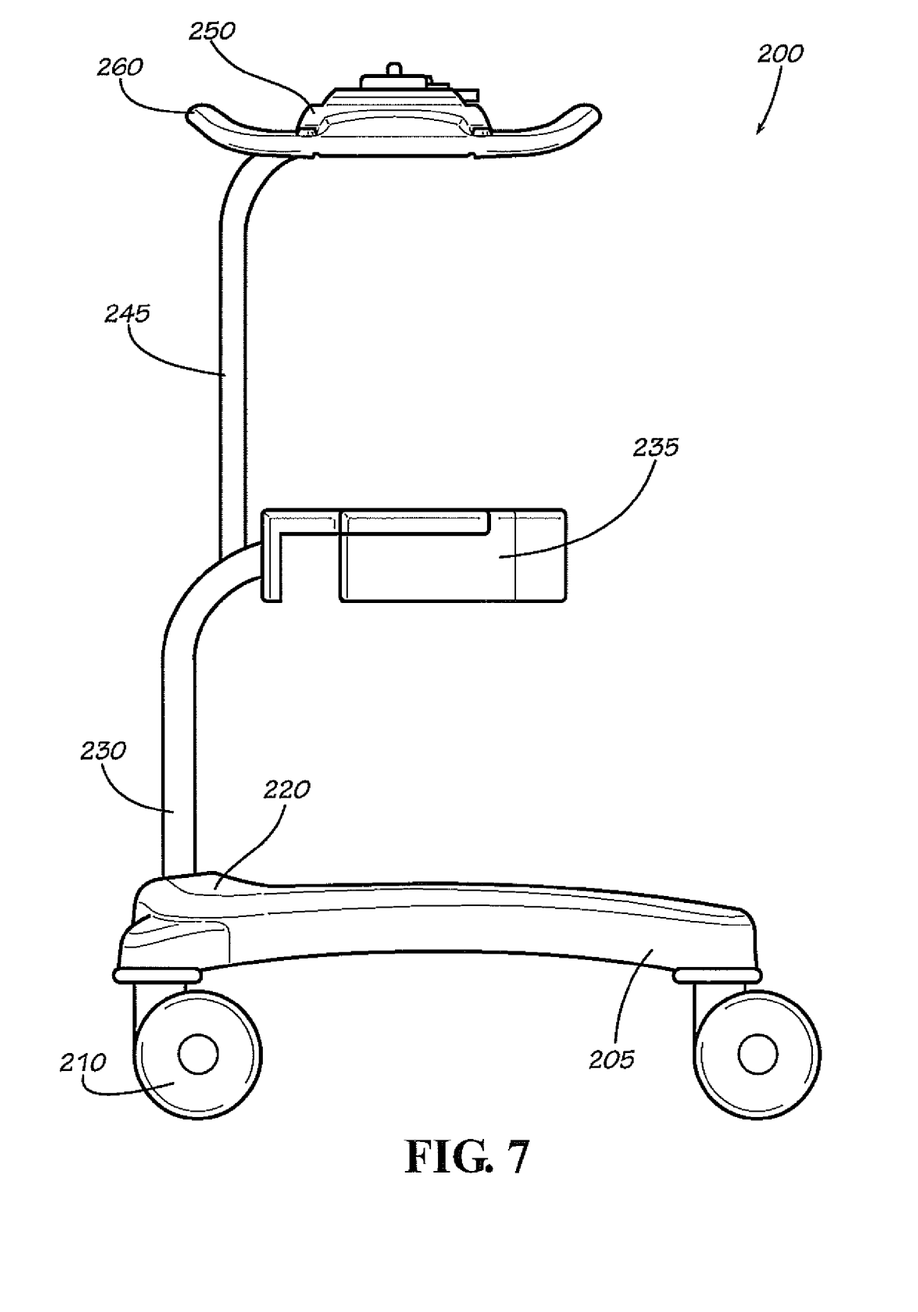
FIG. 7 illustrates a right side elevation view of the compressor-mount medical ventilator cart of FIG. 5 without ventilator components.

Consistent with embodiments of the invention, an extendable arm 270 may be removably attached to the display platform 250, illustrated on the left side of the display monitor 265 in the front view of FIG. 5. The extendable arm 270 may be removably attached to any position on the display platform 250 or, alternatively, to any position on the cart handgrip 260. The extendable arm 270 may be provided with one or more clips or pegs to which papers, clip boards, ventilator tubing or other equipment may be removably attached to the compressor-mount ventilator cart 200. It is contemplated that more than one extendable arm 270 can be utilized with the cart 200.

Each component on the compressorless ventilator cart 100 and the compressor-mount ventilator cart 200 may be added to, removed from, and supported by the respective cart features/elements independently. For instance, the compressor 225 may be removed without having to adjust or remove the BDU 240. Likewise, at any time, the display monitor 265 and the BDU 240 may be added independently to, or removed independently from, the compressor-mount ventilator cart 200 without having to remove, disturb, rearrange, etc., any other components on the cart. Moreover, the BDU platform 235 and the display platform 250 may be removed from the first spine support 230 and the second spine support 245, respectively, without necessitating the removal of other components and/or platforms.

Referring again to FIGS. 6-7, the first spine support 230 and the second spine support 245 may be in the form of inverted "J" shaped members. One end of the first spine support 230 may connect to the "U" shaped base 205 and/or the compressor platform 220, while the other end preferably connects to the BDU platform 235. One end of the second spine support 245 may connect to the first spine support 230, while the other end preferably connects to the display platform 250 or the handgrip 260. Consistent with embodiments of the invention, the second spine support 245 may be removed from the first spine support 230 without impacting the ability of the compressor-mount ventilator cart 200 to support the BDU 240 or the compressor 225. Likewise, it is contemplated that the first spine support 230 may be removed with or without the prior removal of the second spine support 245.

Medical ventilator carts consistent with embodiments of the present invention, whether the compressorless ventilator cart 100 or the compressor-mount ventilator cart 200 discussed above, or otherwise, may comprise cords, cables, connectors, and the like, as is necessary for appropriate use in hospital or medical environments. One or more cords, cables, connectors, etc., may be exposed on the exterior of the cart and its components. Additionally, or alternatively, one or more cords, cables, connectors, etc., may be integrated and hidden within the cart assembly, for instance, to improve the ease of cleaning the cart and its components, to reduce the possible of exposed cords getting snagged on other pieces of equipment, and so forth.

The components or elements of the compressorless ventilator cart 100 and the compressor-mount ventilator cart 200 may be constructed of various metals and plastics (e.g., thermoplastics, thermosets, including foams), and combinations of these materials. The material(s) used to produce any component or element may be selected based on many factors, including cost, weight, durability, resistance to chemicals in hospital and medical environments, ergonomics, and aesthetics, among other factors. For instance, certain components or elements (e.g., the cart handgrip) may have different colors for aesthetic or ease of use considerations.

The elements of the compressorless ventilator cart 100 and the compressor-mount ventilator cart 200 may be attached, affixed, or fastened together with screws, nuts and bolts, tabs, rivets, solder, welding, adhesives, glues, and the like, or combinations thereof, as well as other methods of fastening that would be recognized by one of skill in the art.

In some embodiments, any elements depicted in FIGS. 1-4 relating to the compressorless ventilator cart 100 may be employed in conjunction with the compressor-mount ventilator cart 200. For instance, a humidifier bracket similar to the humidifier bracket 141 on the compressorless ventilator cart 100 may be attached to the BDU platform 235 on the compressor-mount ventilator cart 200. Likewise, any elements depicted in FIGS. 5-8 relating to the compressor-mount ventilator cart 200 may be employed in conjunction with the compressorless ventilator cart 100.

While certain embodiments of the invention have been described, other embodiments may exist. Furthermore, while the specification has been described in language specific to structural features, elements, and/or components, the claims are not limited to the features, elements, and/or components described above. Rather, the specific features, elements, and/or components described above are disclosed as illustrative embodiments of the invention.

What is claimed is:

1. A medical ventilator cart for supporting components of a ventilator system comprising:
   a base comprising a plurality of wheels;
   a first vertical support attached to the base and a first ventilator component platform; and
   a second vertical support attached to a rear of a second ventilator component platform and further attached to a rear of one of the first ventilator component platform and the first vertical support, wherein the second ventilator component platform comprises a plurality of arms, and wherein the plurality of arms attach at multiple locations along a circumference of a handgrip that encircles the second ventilator component platform.

2. The medical ventilator cart of claim 1, wherein components of the ventilator system may be independently removed from the first and the second ventilator component platforms.

3. The medical ventilator cart of claim 2, wherein the first ventilator component platform is adapted to mount a Breath Delivery Unit.

4. The medical ventilator cart of claim 3, wherein the second ventilator component platform is adapted to mount a display monitor.

5. The medical ventilator cart of claim 4, further comprising a battery housing attached to an underside of the base.

6. The medical ventilator cart of claim 4, wherein the base is adapted to mount a compressor below the first ventilator component platform.

7. The medical ventilator cart of claim 4, wherein the base is shaped and the first vertical support is attached to a center of the base.

8. The medical ventilator cart of claim 4, wherein the base is U-shaped and the first vertical support is attached to a rear end of the base.

9. The medical ventilator cart of claim 1, wherein the second vertical support is a spine support.

10. A medical ventilator cart for supporting components of a ventilator system comprising:
   a shaped base comprising a plurality of wheels;
   a first vertical support attached to the base and a first ventilator component platform, wherein the first vertical support extends from a center of the base; and
   a second vertical support attached to a rear of the first ventilator component platform and a rear of a second ventilator component platform, wherein the second ventilator component platform comprises a plurality of arms, and wherein the plurality of arms attach at multiple locations along a circumference of a handgrip that encircles the second ventilator component platform.

11. The medical ventilator cart of claim 10, wherein:
   the first ventilator component platform is adapted to mount a Breath Delivery Unit; and
   the second ventilator component platform is adapted to mount a display monitor.

12. The medical ventilator cart of claim 11, further comprising a battery housing attached to an underside of the base.

13. The medical ventilator cart of claim 11, further comprising a cylinder mount attached to a rear section of the base, wherein the cylinder mount is adapted to hold at least one air cylinder.

14. The medical ventilator cart of claim 10, wherein the second vertical support is a spine support.

15. A medical ventilator cart for supporting components of a ventilator system comprising:
   a U-shaped base comprising a plurality of wheels;
   a first vertical support attached to the base and a first ventilator component platform, wherein the first vertical support extends from a rear end of the base; and
   a second vertical support attached to a rear of the first vertical support and a rear of a second ventilator component platform, wherein the second ventilator component platform comprises a plurality of arms, and wherein the plurality of arms attach at multiple locations along a circumference of a handgrip that encircles the second ventilator component platform; and
   wherein the base further includes a compressor platform adapted to mount a compressor below the first ventilator component platform.

16. The medical ventilator cart of claim 15, wherein:
   the first ventilator component platform is adapted to mount a Breath Delivery Unit; and
   the second ventilator component platform is adapted to mount a display monitor.

17. The medical ventilator cart of claim 16, wherein the first ventilator component platform includes at least one raised rail adapted to be received within a groove of the Breath Delivery Unit to releasably secure the Breath Delivery Unit to the first ventilator component platform.

18. The medical ventilator cart of claim 16, further comprising a cylinder mount attached to the first vertical support, wherein the cylinder mount is adapted to hold at least one air cylinder.

19. The medical ventilator cart of claim 15, wherein the second vertical support is a spine support.

* * * * *